United States Patent
Johannes et al.

(10) Patent No.: US 9,802,868 B2
(45) Date of Patent: Oct. 31, 2017

(54) SHAPED SINTERED CERAMIC BODIES COMPOSED OF Y2O3-STABILIZED ZIRCONIUM OXIDE AND PROCESS FOR PRODUCING A SHAPED SINTERED CERAMIC BODY COMPOSED OF Y2O3-STABILIZED ZIRCONIUM OXIDE

(71) Applicant: Fraunhofer-Gesellschaft zur Foerderung der angewandten Forschung e. V., Munich (DE)

(72) Inventors: Martina Johannes, Hermsdorf (DE); Jens Schneider, Weimar (DE)

(73) Assignee: FRAUNHOFFER-GESELLSCHAFT ZUR FOERDERUNG DER ANGEWANDTEN FORSCHUNG E. V., Munich (DE)

( * ) Notice: Subject to any disclaimer, the term of this patent is extended or adjusted under 35 U.S.C. 154(b) by 367 days.

(21) Appl. No.: 14/381,282

(22) PCT Filed: Mar. 1, 2013

(86) PCT No.: PCT/DE2013/100079
§ 371 (c)(1),
(2) Date: Aug. 27, 2014

(87) PCT Pub. No.: WO2013/127398
PCT Pub. Date: Sep. 6, 2013

(65) Prior Publication Data
US 2015/0118648 A1    Apr. 30, 2015

(30) Foreign Application Priority Data
Mar. 1, 2012   (DE) .......................... 10 2012 101741

(51) Int. Cl.
*C04B 35/48*       (2006.01)
*C04B 35/486*      (2006.01)
(Continued)

(52) U.S. Cl.
CPC ............... *C04B 35/48* (2013.01); *A61C 5/77* (2017.02); *A61C 13/0022* (2013.01);
(Continued)

(58) Field of Classification Search
CPC ...... C04B 35/486; C04B 35/48; C04B 35/482
See application file for complete search history.

(56) References Cited

U.S. PATENT DOCUMENTS

| | | | |
|---|---|---|---|
| 4,279,655 A * | 7/1981 | Garvie | ...................... B21C 3/02 |
| | | | 264/661 |
| 4,506,024 A | 3/1985 | Claussen et al. | |

(Continued)

FOREIGN PATENT DOCUMENTS

| | | |
|---|---|---|
| EP | 0908425 A1 | 4/1999 |
| JP | S61219756 A | 9/1986 |

(Continued)

OTHER PUBLICATIONS

Munoz-Saldana J. et al.: Journal of Materials Research, vol. 18, 2003, pp. 2415-2426.
(Continued)

Primary Examiner — Noah Wiese
(74) Attorney, Agent, or Firm — Abel Law Group, LLP

(57) ABSTRACT

Disclosed is a ceramic sintered shaped body containing $Y_2O_3$-stabilized zirconia with a sintered density of at least 99% of the theoretical sintered density and having a mean grain size of <180 nm. The zirconia fraction of the sintered shaped body comprises tetragonal and cubic phases. Also disclosed is a process for the production of a ceramic sintered shaped body containing $Y_2O_3$-stabilized zirconia, which process comprises dispersion of a submicron powder and comminution of the dispersed submicron powder by means of grinding media having a diameter of less than or equal to 100 µm to a particle size $d_{95}$ of <0.42 µm; shaping
(Continued)

of the dispersion to form a body, and sintering of the body to form the sintered shaped body.

20 Claims, 7 Drawing Sheets

(51) Int. Cl.
    *C04B 35/488* (2006.01)
    *C04B 35/626* (2006.01)
    *C04B 35/645* (2006.01)
    *A61L 27/10* (2006.01)
    *A61C 13/00* (2006.01)
    *C04B 35/64* (2006.01)
    *A61C 5/77* (2017.01)
    *A61C 5/70* (2017.01)

(52) U.S. Cl.
    CPC ............ *A61L 27/10* (2013.01); *C04B 35/486* (2013.01); *C04B 35/4885* (2013.01); *C04B 35/6261* (2013.01); *C04B 35/64* (2013.01); *C04B 35/6455* (2013.01); *A61C 5/70* (2017.02); *C04B 2235/3217* (2013.01); *C04B 2235/3225* (2013.01); *C04B 2235/3244* (2013.01); *C04B 2235/3246* (2013.01); *C04B 2235/5409* (2013.01); *C04B 2235/5445* (2013.01); *C04B 2235/608* (2013.01); *C04B 2235/6027* (2013.01); *C04B 2235/656* (2013.01); *C04B 2235/77* (2013.01); *C04B 2235/782* (2013.01); *C04B 2235/785* (2013.01); *C04B 2235/80* (2013.01); *C04B 2235/96* (2013.01); *C04B 2235/9669* (2013.01); *Y10T 428/268* (2015.01)

(56) References Cited

U.S. PATENT DOCUMENTS

| | | | | |
|---|---|---|---|---|
| 4,659,680 | A * | 4/1987 | Guile | .................. C04B 35/486 264/662 |
| 4,975,397 | A * | 12/1990 | Dworak | ................ C04B 35/486 501/103 |
| 5,958,311 | A | 9/1999 | Ghosh et al. | |
| 6,087,285 | A * | 7/2000 | Oomichi | ................ C04B 35/486 501/103 |
| 8,598,058 | B2 * | 12/2013 | Mathers | .................. B82Y 30/00 106/35 |
| 8,877,664 | B2 | 11/2014 | Ito et al. | |
| 2011/0230340 | A1 | 9/2011 | Binner et al. | |
| 2012/0214661 | A1 | 8/2012 | Ito et al. | |
| 2012/0277088 | A1* | 11/2012 | Mathers | ................ B82Y 30/00 501/134 |

FOREIGN PATENT DOCUMENTS

| | | |
|---|---|---|
| JP | H06305731 A | 11/1994 |
| JP | H11240757 A | 9/1999 |
| JP | 2009286657 A | 12/2009 |
| WO | 2010061196 A2 | 6/2010 |
| WO | 2011121698 A1 | 2/2011 |
| WO | WO/2011/082022 * | 7/2011 ............. C04B 35/48 |

OTHER PUBLICATIONS

Gustavo Suarez et al: "Effect of starting powders on the sintering of nanostructures ZrO2 ceramics by colloidal processing", Science and Technology of Advanced Materials, vol. 10, No. 2, Apr. 1, 2009, 025004.

Suarez et al.: Journal of Nanoscience and Nanotechnology, vol. 10, 2010, pp. 6634-6640.

Hahn, International Tables for Crystallography, 5th ed. vol. A, corrected reprint 2005, pp. 1-911.

San-Yuan Chen et al., "Low-temperature ageing map for 3mol% Y2O3—ZrO2", Journal of Materials Science 24 (1989), pp. 453-456.

Tsukuma et al., "Thermal and Mechanical Properties of Y2)3-Stabilized Tetragonal Zirconia", Science and Technology of Zirconia 11 (1984), pp. 382-390.

Kern, "2.75Yb-TZP Ceramics with High Strength and Aging Resistance", J. Ceram. Sci. Tech., 02[03], pp. 147-154 (2011).

Klimke et al., "Transparent Tetragonal Yttria-Stabilized Zirconia Ceramics: Influence of Scattering Caused by Birefringence", J. Am. Ceram. Soc. 94[6], pp. 1850-1858 (2011).

\* cited by examiner

| Sample | Composition | Grinding ball diameter |
|---|---|---|
| Z-1 | TZ3Y SE | 500 μm |
| Z-2 | TZ3Y SE | 100 μm |
| ZA-10 | 90 wt.-% TZ3Y SE<br>10 wt.-% TM DAR | 100 μm |

Fig. 1

| phase | Z-1 | | Z-2 | | ZA-10 | |
|---|---|---|---|---|---|---|
| | Weight % | $d_{xrd}$ [nm] | Weight % | $d_{xrd}$ [nm] | Weight % | $d_{xrd}$ [nm] |
| $ZrO_2$ tetragonal | 75.9 ± 1.6 | 280 ± 45 | 83.2 ± 1.8 | 154 ± 18 | 77.6 ± 1.7 | 108 ± 10 |
| $ZrO_2$ cubic | 23.5 ± 1.6 | 22 ± 2 | 15.7 ± 1.9 | 11 ± 1 | 11.7 ± 1.7 | 12 ± 2 |
| $ZrO_2$ monoclinic | 0.0 | | 0.3 ± 0.2 | | 0.3 ± 0.2 | |
| $Zr_3Y_4O_{12}$ | 0.6 ± 0.3 | | 0.9 ± 0.3 | | 1.0 ± 0.3 | |
| $Y_2O_3$ | 0.0 | | 0.0 | | 0.0 | |
| $Al_2O_3$ | | | | | 9.4 ± 0.5 | 80 ± 10 |

Fig. 7

| | | Z-1 | Z-2 | ZA-10 |
|---|---|---|---|---|
| Bending strength | MPa | 1300 ± 100 | 1100 ± 170 | 1700 ± 100 |
| Weibull modulus m | - | 13 | 9 | 14 |
| Microhardness HV0.1 | GPa | 14.3 ± 0.7 | 20.4 ± 0.9 | 18.9 ± 2.0 |
| Microhardness HV10 | GPa | 13.28 ± 0.05 | 14.00 ± 0.03 | 15.28 ± 0.07 |
| Fracture toughness (SEVNB) | MPa/m$^2$ | 8.8 ± 0.3 | 10.3 ± 0.6 | 9.1 ± 0.7 |
| Fracture toughness (Anstis) | MPa/m$^2$ | 3.4 | 3.6 | 3.6 |
| Fracture toughness (Niihara) | MPa/m$^2$ | 4.6 | 4.8 | 4.7 |
| Transformability m-ZrO$_2$ on the fracture surface | Weight % | 10.5 | 2.5 | 2.9 |

Fig. 8

SHAPED SINTERED CERAMIC BODIES COMPOSED OF Y2O3-STABILIZED ZIRCONIUM OXIDE AND PROCESS FOR PRODUCING A SHAPED SINTERED CERAMIC BODY COMPOSED OF Y2O3-STABILIZED ZIRCONIUM OXIDE

BACKGROUND OF THE INVENTION

1. Field of the Invention

The invention is directed to a sintered shaped ceramic body formed of $Y_2O_3$-stabilized zirconia and to a process for producing a sintered shaped ceramic body formed of $Y_2O_3$-stabilized zirconia such as are known generically from the publication by Muñoz-Saldaña J., et al. (2003, *Journal of Materials Research* 18, 2415-2426).

2. Discussion of Background Information

Zirconia ($ZrO_2$) is a ceramic that is used, for example, as a refractory ceramic, as a technical ceramic and in prosthetics. The crystal structure of zirconia is classified in accordance with the crystal systems commonly used for the domain of crystallography. These crystal systems are listed, for example, in Hahn, T. (1983: International Table for Crystallography, Reidel, Dordrecht).

Tetragonal stabilized zirconia (hereinafter for brevity called TZP) is one of the strongest high-performance ceramics on the market. TZP ceramics are used, for example, in mechanical engineering, as bioceramics and for household articles.

Certain metal oxides such as $Y_2O_3$ (yttrium oxide), CaO (calcium oxide), MgO (magnesium oxide) or $CeO_2$ (ceric oxide) are used in small concentrations for doping in order to stabilize the tetragonal phase. The highest strengths are achieved with 3 mol % $Y_2O_3$-doped zirconia. For this reason, it is also called 3Y-TZP. The tetragonal phase is metastable in this material, i.e., it is not thermodynamically stable, but a transformation to the monoclinic phase is kinetically inhibited. At room temperature, a phase transition of this type without external influences within finite times does not take place.

The strength of 3Y-TZP and other Y-TZPs derives from what is known as transformation toughening, where the tetragonal phase transforms to the monoclinic phase under the influence of mechanical stresses before a fracture of the material occurs. In so doing, the fracture energy is consumed and compressive stresses are induced in the material. These compressive stresses can counteract further crack propagation. Therefore, the strength of the material depends upon the thermodynamic instability of the tetragonal phase and on the parameters causing the phase transformation.

However, the instability of the tetragonal phase does not only have a positive effect on the behavior of the material. In a moist environment, e.g., in water or in air saturated with water vapor, the phase transformation already takes place spontaneously at temperatures of <100° C. In this case, the tetragonal phase transforms spontaneously into the monoclinic phase. This process is known as "hydrothermal aging" or "low temperature degradation". Hydrothermal aging depends on the temperature and on the concentration of water molecules in the surrounding atmosphere.

Hydrothermal aging always starts at the surface of the material and progresses at a relatively constant rate into the volume of the material. Initially, areas near the surface are affected so that roughness increases and the hardness of the material decreases. Particularly in components with polished surfaces or in wear couples, enormous economic losses are caused by hydrothermal aging. The life of these components is appreciably reduced. While hydrothermal aging has no noticeable effect on component strength in components with a high volume-to-surface ratio, it results in catastrophic failures particularly for components having a surface which performs a specific function.

In dental restorations comprising 3Y-TZP, the translucency of the material plays an important role for aesthetic reasons. Therefore, efforts are made to produce crown frameworks and bridge frameworks of 3Y-TZP, for example, with high translucency as well as high hydrothermal resistance. Heretofore, these requirements could be reconciled only to a limited extent.

Over the past decade, considerable efforts have been made to increase the hydrothermal stability of 3Y-TZP. This can be accomplished in principle by an increase in the amount of stabilizer contained in the material; a homogeneous distribution of the stabilizer in the matrix of the material, by reducing the grain size, and by the addition of $Al_2O_3$ of ≥0.25 mass %. The increased stabilizer content leads to a deterioration of the mechanical properties. The addition of $Al_2O_3$ according to manufacturer's specifications leads to increased hydrothermal stability, but the translucency of the ceramic is substantially reduced because of scattering phenomena.

It is known that the tetragonal phase can be stabilized when the grain size is below a critical value. The critical grain size is specified at 360 nm in Muñoz-Saldaña et al. (2003), at 370 nm in Chen et al. (1989: *Journal of Materials Science* 24(2): 453-456) and at 400 nm in Tsukuma et al. (1984: *Science and technology of zirconia* 11: 382-390). Other authors report that the TZP ceramic prepared by them with a grain size of 200 nm was not aging-stable (Kern et al, 2011: *Journal of Ceramic Science and Technology* 2(3): 147-154).

The publication by Suárez et al. (2009: *Science and Technology of Advanced Materials* 10(2): 25004) discloses sintered shaped bodies with mean grain sizes of about 100 nm which are exclusively in tetragonal phase and were produced from nanopowders with particle sizes of 65 nm.

As defined by the EU Commission of Oct. 18, 2011, nanomaterials are materials with particle sizes of less than 100 nm (e.g., nanoparticles, nanoplates or nanofibers).

The preparation of an aging-stabilized 3Y-TZP comprising commercial nanopowders with a particle size of the nanopowder of 65 nm is known from WO 2010/061196 A2.

The known processes have the drawback that they use expensive nanopowders making it impossible to produce aging-stable sintered shaped bodies inexpensively.

The use of 50 µm size grinding media for deagglomeration of nanopowders is known from the publications by Suarez et al., (Suarez et al., 2010, *Journal of Nanoscience and Nanotechnology* 10: 6634-6640, and Suarez et al., 2009, *Science and Technology of advanced Materials* 10, doi: 10/1088/1468-6996/10/2/025004). Agglomerates are formed when nanopowder is stored over extended periods of time. The tendency of nanopowders to form such agglomerates is another drawback to their use.

The transmission of visible light is sharply reduced in Y-TZPs because of the birefringence of tetragonal zirconia. According to Klimke et al. (2011: *Journal of the American Ceramic Society* 94 (6), 1850-1858), a theoretical inline transmission of about 7% can be measured at a wavelength of 550 nm by reducing the grain size to 150 nm. The human eye has the greatest sensitivity at this wavelength.

Muñoz-Saldaña et al. have shown that an aging-stable 3Y-TZP ceramic with a mean grain size of 320 nm and a three point bending strength of 1400 MPa can be realized with commercial submicron powder.

SUMMARY OF THE INVENTION

It is the object of the invention to propose an aging-stable sintered shaped body. The invention has the further object of proposing a possibility for producing aging-stable sintered shaped bodies which is more economical and process-efficient compared to the prior art.

This object is met by a ceramic sintered shaped body containing $Y_2O_3$-stabilized zirconia with a sintered density of at least 99% of the theoretical sintered density. A sintered shaped body according to the invention is characterized in that the sintered shaped body has a mean grain size of <180 nm;

the zirconia fraction of the sintered shaped body comprises at least 98 mass % tetragonal phase and cubic phase; and the sintered shaped body has a monoclinic fraction of less than 3 mass % after 120 hours at 134° C. and 2 bar in water vapor atmosphere. The sintered shaped body has a grain size preferably between 150 nm and 170 nm.

In a further embodiment of the sintered shaped body, this sintered shaped body contains 2-15 mass % of unstabilized zirconia. The unstabilized zirconia is preferably in tetragonal phase. Through the partial substitution of 3 mol % of $Y_2O_3$-stabilized zirconia by unstabilized zirconia, the effective stabilizer content in the zirconia phase is reduced, which can lead to increased strength and fracture toughness.

The zirconia fraction of the sintered shaped body is 75-95 mass % in the tetragonal phase and 5-25 mass % in the cubic phase. A monoclinic zirconia fraction of <2 mass % may be provided. The zirconia fraction comprises $Y_2O_3$-stabilized zirconia and unstabilized zirconia. The phase composition can be determined from x-ray diffraction data using Rietveld refinement.

A further embodiment of the sintered shaped body according to the invention which is advantageous for specific application of the sintered shaped body, for example, for dental implants and structures results when an optical transmission at a wavelength of 550 nm and with a thickness of 0.5 mm of the material of the sintered shaped body is at least 7%. The optical transmission is indicated here in a simplified manner for a wavelength of 550 nm at which the eye possesses its greatest sensitivity in daylight.

It is possible that the sintered shaped body contains 0.2-20 mass % of $\alpha$-$Al_2O_3$.

The sintered shaped body according to the invention can be subjected to hot isostatic pressing. In an embodiment of the sintered shaped body, the sintered shaped body is subjected to hot isostatic pressing and has a sintered density of >6.04 g/cm$^3$.

The sintered shaped body has a four point bending strength of at least 1000 MPa. The four point bending strength is determined in accordance with DIN EN 843-1. In this regard, the dense sintered shaped body of 100% 3Y-TZP has a four point bending strength of >1000 MPa and a microhardness HV 0.1 according to DIN EN 843-4 of >13 GPa. Sintered shaped bodies of 90% 3Y-TZP and 10% $\alpha$-$Al_2O_3$ achieve strengths of about 1700 MPa and a microhardness HV 0.1 of >18 GPa.

The above-stated object is further met by a process for the production of a ceramic sintered shaped body containing $Y_2O_3$-stabilized zirconia. The process includes the steps of:

dispersion of a submicron powder with a fraction of at least 65 mass % of the $Y_2O_3$-stabilized zirconia, comminution of the dispersed submicron powder by means of grinding media having a diameter of less than or equal to 100 μm to a particle size $d_{95}$ of less than 0.42 μm, shaping of the dispersion of the comminuted submicron powder to form a body, and sintering of the body to form the sintered shaped body.

The submicron powder can contain additional substances. For instance, 0.2-20 mass % of $\alpha$-$Al_2O_3$ or unstabilized zirconia or a mixture of these substances can be contained in further embodiments of the process according to the invention.

The comminution of the dispersed submicron powder is preferably carried out in an agitator ball mill by means of grinding media having a diameter of less than or equal to 100 μm. The production process involves the dispersion of the powder preferably in water with the aid of a suitable stabilizer to a solids fraction of 70 mass %. The submicron powder is preferably comminuted to a particle size $d_{95}$ between 0.250 and 0.420 μm (measured by sedimentation analysis). This ensures that the process is carried out in an efficient manner.

The dispersion of the powder can also be carried out in other solvents or mixtures of solvents and using at least one dispersant.

Also, agglomerates and aggregates in the submicron powder are extensively eliminated by the comminution. A stable slurry that can be processed over a number of days is formed by the particles dispersed in the aqueous phase.

Modern, instrumented agitator ball mills afford the possibility of tracking energy input during the grinding process and, therefore, obtaining reproducible grinding results as a function of the solids mass. Modern separating systems allow the use of very small grinding media with diameters of less than 100 μm. The latter make it possible to achieve small particle sizes and a very narrow particle size distribution in the slurry with slightly agglomerated raw materials. The throughput of the mill can range from 80 kg to 150 kg solids per hour and is accordingly on an order of magnitude for industrial use.

The submicron powder to be dispersed preferably has a specific surface area of less than 20 m$^2$/g.

The shaping of the dispersion to form a body is preferably carried out by slip casting. The shaping is realized by slip casting in plaster molds. The green density of the cast shaped body is <60% of the theoretical sintered density without isostatic pressing of the green bodies.

Shaping is also possible by pressing of granules (isostatic, uniaxial).

The sintering of the body to form the sintered shaped body is carried out at a sintering temperature of between 1200° C. and 1350° C., preferably at a sintering temperature of between 1250° C. and 1300° C. The sinter activity of the powder is so high after comminution that the green body can be sintered at the comparatively low sintering temperatures and a sintered density of at least 95% of the theoretical sintered density is achieved subsequently.

In a further embodiment of the process according to the invention, the sintered shaped body is subjected to hot isostatic recompression at a temperature of between 1200° C. and 1350° C., preferably between 1250° C. and 1330° C. A sintered density of at least 99% of the theoretical sintered density is achieved. The theoretical density is calculated starting from a density of 6.1 g/cm$^3$ for 3Y-TZP and 3.98 g/cm$^3$ for $\alpha$-$Al_2O_3$.

The sintered shaped body produced in this way has a grain size of <180 nm, preferably between 15 nm and 170 nm, and shows no hydrothermal aging after exposure for 120 hours at 134° C. and 2 bar in a water vapor atmosphere. The structural characteristics of the sintered shaped body produced by the process according to the invention have the effect that the sintered shaped body produced in this way has high aging stability against hydrothermal affects. The monoclinic phase fraction after exposure for 120 hours is less than 3 mass %, but preferably less than 2 mass %.

The dense sintered shaped bodies of 100% 3Y-TZP have a four point bending strength of >1000 MPa and a microhardness HV 0.1 of >13 GPa. Sintered shaped bodies of 90% 3Y-TZP and 10% $\alpha$-$Al_2O_3$ achieve strengths of about 1700 MPa and a microhardness HV 0.1 of >18 GPa.

The advantages of the material and process according to the invention reside in the use of commercial submicron powder in combination with an optimized comminution process using very small grinding media. Accordingly, aggregates and agglomerates are optimally comminuted and the particles are dispersed in a highly concentrated slurry which is suitable for shaping by means of slip casting. The fine particles are very narrowly distributed, which provides the basis for a high sinter activity and a fine, very homogeneous structure.

The process according to the invention allows a high degree of economic efficiency in the production of ceramic sintered shaped bodies from a $Y_2O_3$-stabilized zirconia. The favorable prices of raw materials for submicron powder contribute to this. The preparation process by means of agitator ball mills is capable of scale-up and can be transferred from laboratory scale to industrial standards.

The material properties of the sintered shaped body according to the invention can be understood, for example, with reference to a specimen material. The chemical composition and crystal composition, the grain size, the sintered density and the strength of the material can be examined for this purpose. The grain size and the type of continuous or dispersed phases can be verified through microstructural analysis by means of scanning electron microscopy. The chemical analysis supplies data about which elements are present in the material of the sintered shaped body. The crystal composition and hydrothermal resistance of the sintered shaped bodies can be tested quantitatively based on x-ray phase analysis and subsequent Rietveld refinement. Another result of the stabilization of the tetragonal phase for preventing hydrothermal aging is that the transformation toughening is inhibited. For fine-grained Y-TZP ceramics produced from nanopowders, this results in reduced strengths compared with ceramics comprising submicron grits.

The sintered shaped body according to the invention is applied wherever Y-TZP can only be used to a very limited extent because of its tendency toward hydrothermal aging. This relates particularly to medical applications such as implants for artificial joints and dental implants. Further, there exists a possibility for use for valves and nozzles in internal combustion engines and as a catalyst support. Liners for pumps for chemically corrosive materials and for conveying media at elevated temperatures are also possible with this material. In particular, this material is suitable for mechanical seals in mixing faucets because of its excellent surface treatability and hydrothermal resistance. The sintered shaped body produced by the process according to the invention and the sintered shaped body according to the invention can be used as a green body for implants. In this regard, it is also possible in principle to use the sintered shaped body as implant without further treatment. It can be used as a green body for dental crown frameworks and bridge frameworks. In the sector of plant and machinery engineering, the sintered shaped body can be used as a component in pumps, for example, for pump liners, or as a component in turbines, where at least some areas of the component can come in contact with water vapor. It is also possible to use the sintered shaped body as a component in internal combustion engines, where at least some areas of the surface of the component can come in contact with liquid fuels, solvents, solvent mixtures, water, water vapor or mixtures thereof, vapors and aerosols. Further uses in which the sintered shaped body is used under conditions promoting hydrothermal aging are advantageous.

BRIEF DESCRIPTION OF THE DRAWINGS

The invention is described more fully in the following with reference to embodiment examples, drawings and tables. The drawings show:

FIG. 1 a first table containing compositions and grinding parameters of investigated sintered bodies;

FIG. 7 a second table containing structure characteristics of examined sintered bodies;

FIG. 8 a third table containing mechanical properties of examined sintered bodies after treating by HIP;

DETAILED DESCRIPTION OF THE INVENTION

Figure 2:
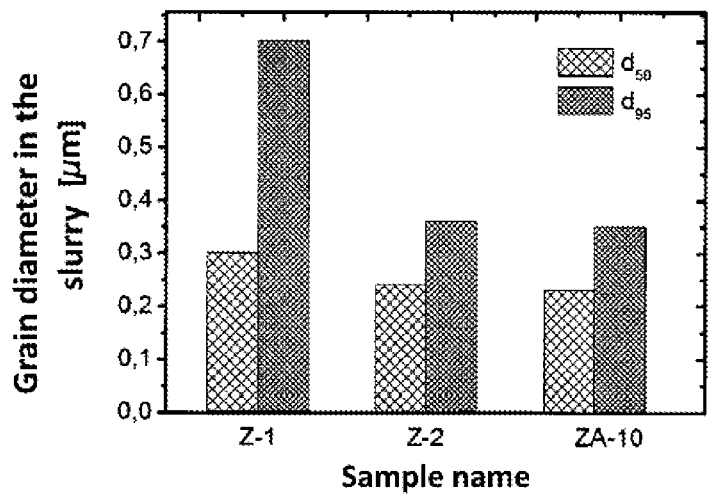
FIG. 2 particle sizes $d_{50}$ and $d_{95}$ which were measured in the slurry after grinding a submicron powder according to the process according to the invention.

Example 1: In a stirring unit, 270 ml of water are placed and a suitable dispersant is added. Next, 500 g of 3Y-TZP powder with a specific surface area of 6 $m^2/g$ are stirred in. The slurry is put in an agitator ball mill. The mill is filled up to 85% by grinding balls having a diameter of 100 μm. The slurry is ground for two hours at 3500 R.P.M., which corresponds to a circumferential speed of 11 m/s, to a particle size distribution characterized in that the $d_{95}$ value is <0.42 μm and the $d_{50}$ value is <0.3 μm.

The milling time is approximately two hours for this amount of solids. The slurry is cast in plaster molds which are dimensioned so as already to make allowances for shrinkage. The standing time is determined by the size of the component. The green bodies are dried in air at 50° C. and then sintered for two hours at 1250° C. The sintered shaped bodies have approximately 95% of the theoretical density. The shaped bodies are then subjected to hot isostatic pressing at 1250° C. and finally have a density of 6.07 $g/cm^3$. This corresponds to 99.5% of the theoretical density.

The mean grain size is determined by means of linear intercept methods in accordance with DIN EN 623-3 and is 160 nm for this material. The strength is 1063 MPa, and the microhardness is 18 GPa. The sintered shaped bodies are aged in a water vapor atmosphere for 120 hours at 134° C. The monoclinic fraction after aging is determined by XRD (X-Ray Diffraction). The samples have a monoclinic phase content of between 0.5% and 3%.

Example 2: In a stirring unit, 270 ml of water are placed and a suitable dispersant is added. Next, 450 g of 3Y-TZP powder and 50 g of α-$Al_2O_3$ powder with a specific surface area of 6 $m^2$/g and 12 $m^2$/g, respectively, are stirred in. The slurry is put in an agitator ball mill.

The mill is filled up to 85% with grinding balls having a diameter of 100 μm. The slurry is ground for two hours at 3500 R.P.M., which corresponds to a circumferential speed of 11 m/s, to a particle size distribution characterized in that the $d_{95}$ value is <0.42 μm and the $d_{50}$ value is <0.30 μm. The milling time is approximately two hours for this amount of solids. The slurry is cast in plaster molds which are dimensioned so as already to make allowances for shrinkage. The standing time is determined by the size of the component. The green bodies are dried in air at 50° C. and then sintered for two hours at 1300° C. The sintered shaped bodies have approximately 95% of the theoretical density. The shaped bodies are then subjected to hot isostatic pressing at 1300° C. and finally have a density of 5.76 g/$cm^3$. This corresponds to 99.5% of the theoretical density of 5.79 g/$cm^3$.

The mean grain size is determined by means of linear intercept methods in accordance with DIN EN 623-3 and is 143 nm for this material. The strength is 1700 MPa. The sintered shaped bodies are aged in a water vapor atmosphere for 120 hours at 134° C. The monoclinic fraction after aging is determined by XRD. The samples have a monoclinic phase content of between 0 and 1%.

EXAMPLE 3: Two 3Y-TZP charges and one ATZ charge (90 wt. % 3Y-TZP/10 wt. % $Al_2O_3$) are prepared. TZ3Y-SE (Tosoh, Japan) and TM-DAR (Taimei Chemicals, Japan) with particle sizes of 70 nm and 100 nm, respectively, were used as raw materials. The powders were dispersed in water using 0.5% ammonium polyacrylate (Zschimmer & Schwarz, Germany) and then ground and dispersed in an agitator ball mill (Mini Cer, Netzsch FMT, Germany) using different grinding ball diameters. Table 1 shows the compositions and the grinding parameters.

The particle size distribution in the slurry was analyzed with an Ultrafine particle analyzer (UPA, Microtrac, USA). Disks were shaped to the dimensions of 3×20×30 mm by slip casting in plaster molds. Subsequently, sintering curves were prepared and the HIP temperatures were derived therefrom. The density of the HIPed sample bodies was determined by the Archimedes principle. The surfaces of the disks were polished with diamond paste. The roughness $R_a$ of the surfaces was between 8.5 and 16 nm. The structures were examined with a FESEM (Zeiss Ultra 55+; Carl Zeiss NTS Germany). The mean grain size was determined by the linear intercept method.

The samples were aged in an autoclave at 134° C. and 2 bar in water vapor for up to 200 h. The phase composition of the aged samples was measured by XRD (D8 Advance, Bruker, Germany) and quantified by Rietveld refinement (AutoQuan, GE-Sensing Technology, Ahrensburg, Germany).

Four point bending strength was tested on 2×2.5×25 mm bending rods in accordance with EN 843-1. Fifteen bending rods were tested and the mean bending strength $\sigma_0$ and Weibull modulus m were then determined.

Sample Z-1 was prepared by a standard procedure and samples Z-2 and ZA-10 were prepared in an optimized process (Table 1). Although the grinding energy in charges Z-2 and ZA-10 is eight times greater than in charge Z-1, smaller particle sizes were measured in the slurry, which is shown in FIG. 1.

It was possible to appreciably reduce the $d_{95}$ value and, therefore, the particle size distribution in the slurry by means of the optimized preparation. This results in a considerable increase in sinter activity, which is illustrated by the sintering curves in FIG. 2.

Sample bodies Z-1 were sintered at 1450° C. without subsequent HIP. Sample bodies Z-2 and ZA-10 were sintered at 1250° C. and 1300° C., respectively, and HIPed at the same temperature. The relative densities of all of the samples were greater than 99.5% of the theoretical densities of 6.1 g/$cm^3$ for 3Y-TZP and 5.79 g/$cm^3$ for ATZ 90/10. The microstructure of the sintered and HIPed sample bodies is shown in FIG. 2.

Figure 3:
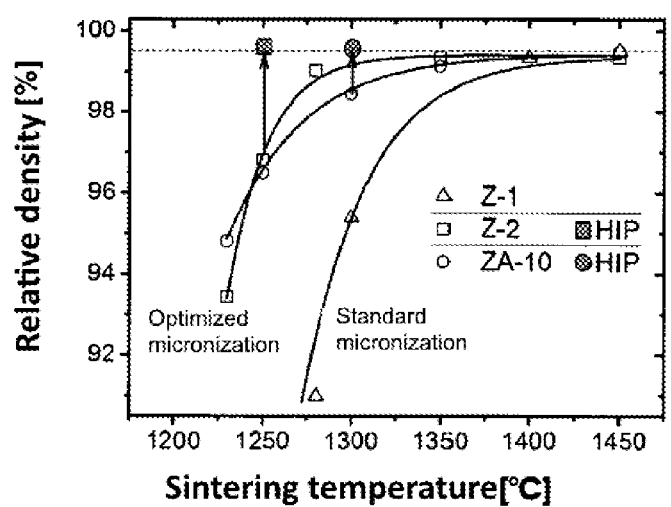
FIG. 3 sintering curves of cast sample bodies with indicated HIP temperature (arrows) and relative density after HIP (hot isostatic pressing) (gray-shaded symbols)

The effect of the optimized preparation can be clearly seen from FIG. 2. The grain sizes can be appreciably reduced by an optimized preparation and the accompanying increase in sinter activity. The grain sizes of the sample bodies are shown in FIG. 3.

Figure 4:
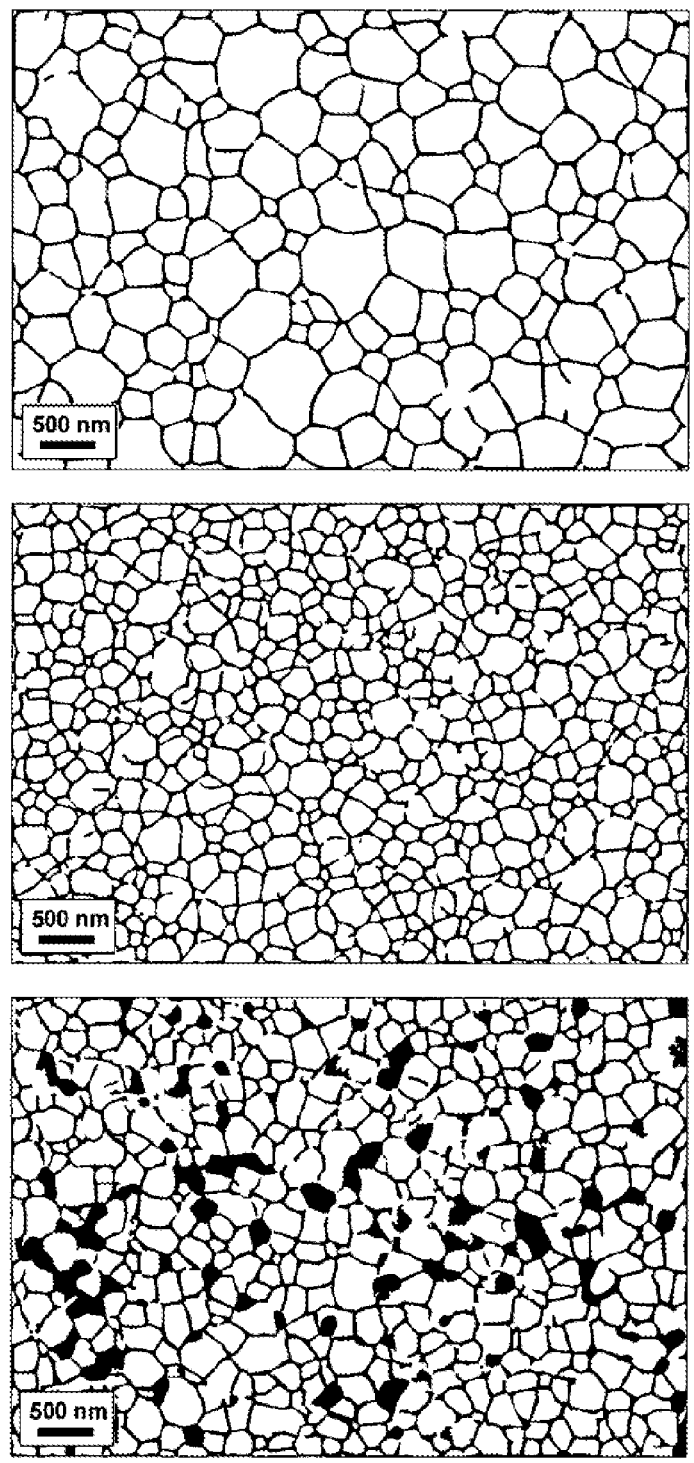
FIG. 4 FESEM pictures of portions of conventional sintered bodies (top, sample Z-1) and sintered bodies according to the invention (center and bottom, samples Z-2 and ZA-10, respectively)

The grain sizes in the dense-sintered ceramics are proportional to the $d_{95}$ value of the particle size distribution in the slurry (compare FIG. 1). The particle size distribution in the slurry is accordingly a key value for the optimization of very fine-grained structures. The aging stability of the ceramics was tested in accelerated aging tests in the autoclave. FIG. 4 shows the monoclinic phase content in the samples as a function of the aging time at 134° C. in water vapor.

Figure 5:
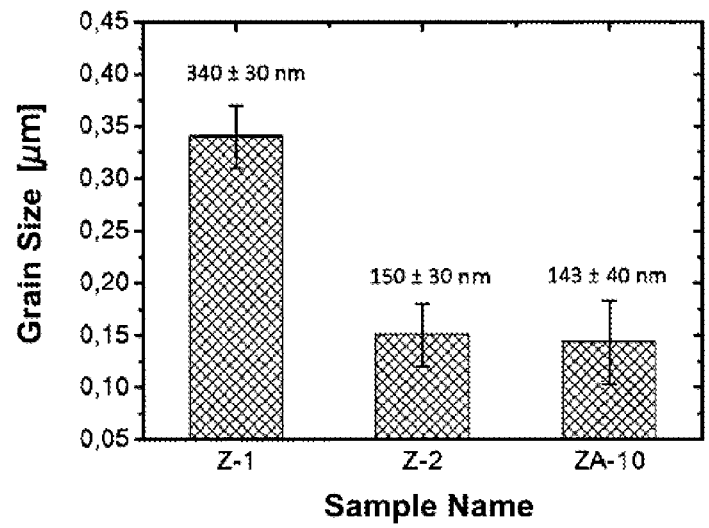
FIG. 5 grain sizes of the sintered bodies.

Sample Z-1 showed a very rapid rise of the monoclinic phase after short aging times. Samples Z-2 and ZA-10 show no rise in the monoclinic phase over the period of study. Accordingly, the ceramics may be designated as aging-stable. It is assumed that the reason for this is the stabilization of the tetragonal phase through the small grain size. This could also affect the strength characteristics of the very fine-grained 3Y-TZP ceramics. The four point bending strength and the Weibull modulus of the 3Y-TZP and ATZ ceramics are shown in FIG. 5.

The strength of the Z-2 ceramic is reduced compared to the Z-1 ceramic. It is assumed that this effect also stems from the stabilization of the tetragonal phase so that the transformation toughening and hydrothermally induced phase transformation are inhibited.

In contrast, the ATZ ceramic ZA-10 has a very high strength of 1700 MPa and a Weibull modulus of 14.3. The addition of $Al_2O_3$ to the Y-TZP matrix compensates for the negative influence of the small grain size and even leads to higher strengths compared with conventionally produced 3Y-TZP ceramic. The reason for this is assumed to be a mechanical stressing of the grains due to thermal mismatch. When cooled after sintering, a local ring tensile stress forms in the Y-TZP matrix around the $Al_2O_3$ grains so that the driving force for the phase transformation is increased locally and can provide for a higher strength of the ceramic. This results in a high-strength, aging-stable dispersion ceramic which is excellently suitable for use as bio-inert implant material.

FIG. 1 contains a table in which are indicated the submicron powder used as starting material for a process according to the invention, the composition of the submicron powder and the diameter of the grinding media (grinding balls) used for the comminution of the respective submicron powder.

FIG. 2 shows the particle sizes contained in the slurry after grinding and measured in $d_{50}$ and $d_{95}$ standards. These size distributions of the particles were achieved through the use of 500-μm grinding media (sample Z-1) and 100-μm grinding media (samples Z-2 and ZA-10).

FIG. 3 shows the resulting sintering curves of cast sample bodies of the submicron powders ground according to the above specifications. The relative density of the obtained sintered bodies is indicated in percent (relative density [%]) and plotted over the sintering temperature in ° C. The temperatures of the hot isostatic pressing (arrows) and the relative densities (gray-shaded symbols) achieved in this way are shown.

FIG. 4 shows FESEM illustrations of the structure of the obtained sintered shaped bodies of samples Z-1 (top), Z-2 (center) and ZA-10 (bottom). The bright grains are zirconium, the dark grains are aluminum.

FIG. 5 shows the grain sizes of the obtained sintered shaped bodies. The grain sizes of the submicron powders comminuted by means of grinding balls having a diameter of 100 μm are substantially lower than the grain size of the submicron powder comminuted by grinding balls having a diameter of 500 μm. The grain size (μm) is plotted over the samples (Sample Name).

Figure 6:
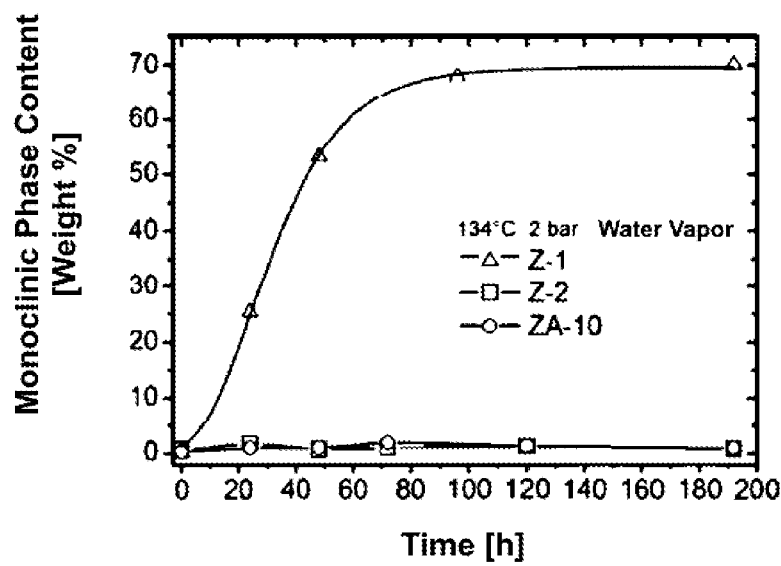
FIG. 6 aging stability of the sintered bodies determined by accelerated aging tests in autoclaves at 134° C. and 2 bar in water vapor.

FIG. 6 shows the monoclinic phase content in percent by weight (wt. %) over time (Aging Time [h]). The sintered shaped bodies were tested under a pressure of 2 bar in water vapor at 134° C. It can be clearly seen that sintered bodies Z-2 and ZA-10 show no increase in monoclinic phase content far in excess of 120 hours (up to at least 192 hours). This means that sintered shaped bodies Z-2 and ZA-10 are aging-stable for over at least 192 hours under water vapor atmosphere. In contrast, Z-1 shows a massive and steep rise in monoclinic phase content of more than 60 mass % and is not stable with respect to hydrothermal aging.

FIG. 7 shows a second table listing material compositions of the dense sintered shaped bodies. The error is indicated as three times the standard deviation (as given by the Rietveld program).

FIG. 8 shows a third table listing the mechanical properties of the sintered shaped bodies after HIP treatment. The properties are: bending strength, Weibull modulus m, microhardness HV0.1, microhardness HV10, fracture toughness (SEVNB), fracture toughness (Anstis), fracture toughness (Niihara) and transformability m-$ZrO_2$ on the fracture surface.

Figure 9:
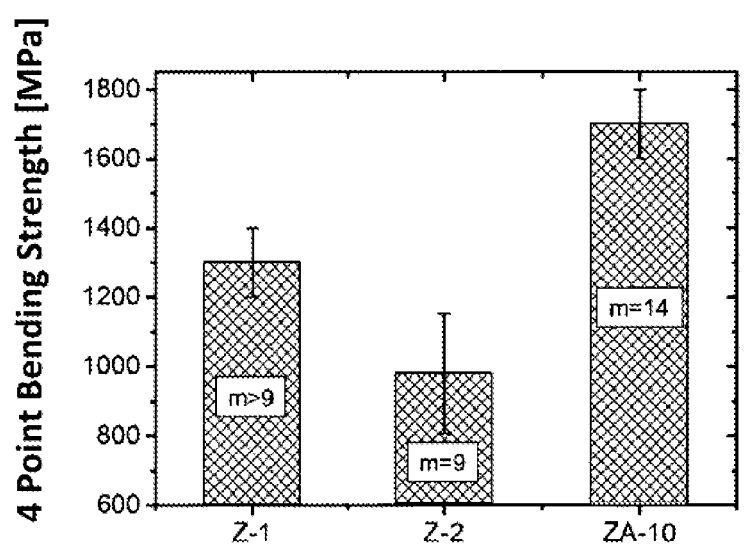
FIG. 9 four point bending strengths and Weibull moduli of examined sintered bodies.

Finally, FIG. 9 shows the four point bending strength [Mpa] of the sintered shaped bodies Z1, Z-2 and ZA-10 and the respective associated Weibull modulus (indicated in the box on each column).

What is claimed is:

1. A ceramic sintered shaped body wherein the sintered shaped body consists of $Y_2O_3$-stabilized zirconia consisting of 97 mol % zirconia and 3 mol % $Y_2O_3$ and having
    a sintered density of at least 99% of a theoretical sintered density;
    a mean grain size of smaller than 180 nm;
    a zirconia fraction comprising tetragonal and cubic phases in a concentration of at least 98 mass %; and
    a monoclinic fraction of less than 3 mass % after 120 hours at 134° C. and 2 bar in a water vapor atmosphere.

2. A ceramic sintered shaped body, wherein the sintered shaped body comprises $Y_2O_3$-stabilized zirconia and 2-15 mass % of unstabilized zirconia and has
    a sintered density of at least 99% of a theoretical sintered density;
    a mean grain size of smaller than 180 nm;
    a zirconia fraction comprising tetragonal and cubic phases in a concentration of at least 98 mass %; and
    a monoclinic fraction of less than 3 mass % after 120 hours at 134° C. and 2 bar in a water vapor atmosphere.

3. The ceramic sintered shaped body of claim 2, wherein the $Y_2O_3$-stabilized zirconia consists of 97 mol % zirconia and 3 mol % $Y_2O_3$.

4. The ceramic sintered shaped body of claim 2, wherein the unstabilized zirconia is present in the tetragonal phase.

5. The ceramic sintered shaped body of claim 2, wherein the shaped body consists of $Y_2O_3$-stabilized zirconia and 2-15 mass % of unstabilized zirconia.

6. The ceramic sintered shaped body of claim 2, wherein 75-95 mass % of the zirconia fraction is present in the tetragonal phase and 5-25 mass % of the zirconia fraction is present in the cubic phase, and wherein a monoclinic fraction of less than 2 mass % is present.

7. A ceramic sintered shaped body, wherein the sintered shaped body comprises $Y_2O_3$-stabilized zirconia and 0.2-20 mass % of $\alpha$-$Al_2O_3$ and has
    a sintered density of at least 99% of a theoretical sintered density;
    a mean grain size of smaller than 180 nm;
    a zirconia fraction comprising tetragonal and cubic phases in a concentration of at least 98 mass %; and
    a monoclinic fraction of less than 3 mass % after 120 hours at 134° C. and 2 bar in a water vapor atmosphere.

8. The ceramic sintered shaped body of claim 7, wherein the $Y_2O_3$-stabilized zirconia consists of 97 mol % zirconia and 3 mol % $Y_2O_3$.

9. The ceramic sintered shaped body of claim 7, wherein the shaped body consists of $Y_2O_3$-stabilized zirconia and 0.2-20 mass % of $\alpha$-$Al_2O_3$.

10. The ceramic sintered shaped body of claim 7, wherein 75-95 mass % of the zirconia fraction is present in the tetragonal phase and 5-25 mass % of the zirconia fraction is present in the cubic phase, and wherein a monoclinic fraction of less than 2 mass % is present.

11. The ceramic sintered shaped body of claim 7, wherein the shaped body has a four point bending strength of at least 1000 MPa.

12. A process for the production of the ceramic sintered shaped body of claim 2, wherein the process comprises:
    dispersing a submicron powder comprising at least 65 mass % of $Y_2O_3$-stabilized zirconia and from 2 to 15 mass % of unstabilized zirconia,
    comminuting dispersed submicron powder by grinding media having a diameter of less than or equal to 100 μm to a particle size $d_{95}$ of less than 0.42 μm,
    shaping a dispersion of comminuted submicron powder to form a body, and
    sintering the shaped body to form the ceramic sintered shaped body.

13. The process of claim 12, wherein the submicron powder has a specific surface area of less than 20 m²/g.

14. The process of claim 12, wherein shaping is carried out by slip casting.

15. The process of claim 12, wherein the body is sintered at a sintering temperature of from 1200° C. to 1350° C.

16. The process of claim 15, wherein the process further comprises subjecting the sintered body to hot isostatic pressing at a temperature of from 1200° C. to 1350° C.

17. A process for the production of the ceramic sintered shaped body of claim 7, wherein the process comprises:
    dispersing a submicron powder comprising at least 65 mass % of $Y_2O_3$-stabilized zirconia and from 0.2 to 20 mass % of $\alpha$-$Al_2O_3$, comminuting dispersed submicron powder by grinding media having a diameter of less than or equal to 100 μm to a particle size $d_{95}$ of less than 0.42 μm, shaping a dispersion of comminuted submicron powder to form a body, and sintering the shaped body to form the ceramic sintered shaped body.

18. The process of claim 17, wherein the submicron powder has a specific surface area of less than 20 m²/g.

19. The process of claim 17, wherein shaping is carried out by slip casting.

20. The process of claim 17, wherein the body is sintered at a sintering temperature of from 1200° C. to 1350° C.

* * * * *